United States Patent
Kojima et al.

(10) Patent No.: US 12,429,451 B2
(45) Date of Patent: Sep. 30, 2025

(54) ION SENSOR AND METHOD FOR MEASURING IONS

(71) Applicants: SYSMEX CORPORATION, Kobe (JP); NATIONAL UNIVERSITY CORPORATION KYOTO INSTITUTE OF TECHNOLOGY, Kyoto (JP)

(72) Inventors: Junko Kojima, Kobe (JP); Kenichi Uchiyama, Kobe (JP); Yumi Yoshida, Kyoto (JP)

(73) Assignees: SYSMEX CORPORATION, Kobe (JP); NATIONAL UNIVERSITY CORPORATION KYOTO INSTITUTE OF TECHNOLOGY, Kyoto (JP)

( * ) Notice: Subject to any disclaimer, the term of this patent is extended or adjusted under 35 U.S.C. 154(b) by 430 days.

(21) Appl. No.: 17/895,118

(22) Filed: Aug. 25, 2022

(65) Prior Publication Data

US 2023/0078290 A1   Mar. 16, 2023

(30) Foreign Application Priority Data

Aug. 30, 2021   (JP) .................................. 2021-140327

(51) Int. Cl.
*G01N 27/333*   (2006.01)

(52) U.S. Cl.
CPC ....... *G01N 27/3335* (2013.01); *G01N 27/333* (2013.01)

(58) Field of Classification Search
CPC ........... G01N 27/3335; G01N 27/4073; G01N 27/333; G01N 27/423; G01N 33/492; G01N 27/30

See application file for complete search history.

(56) References Cited

U.S. PATENT DOCUMENTS

2012/0118762 A1   5/2012   Bakker
2022/0334077 A1   10/2022  Uchiyama et al.

FOREIGN PATENT DOCUMENTS

JP   3394262 B2   4/2003
JP   2004-309478 A   11/2004
(Continued)

OTHER PUBLICATIONS

Komaba et al., "All-solid-state ion-selective electrodes with redox-active lithium, sodium, and potassium insertion materials as the inner solid-contact layer," 2017, Analyst, vol. 142, pp. 3857-3866 (Year: 2017).*

(Continued)

*Primary Examiner* — Luan V Van
*Assistant Examiner* — Kaylee Tseng
(74) *Attorney, Agent, or Firm* — METROLEX IP LAW GROUP, PLLC; Robert L. Scott, Esq

(57) ABSTRACT

The ion sensor of the present invention is a current measurement type ion sensor that measures a current to measure a target ion, and includes an organic phase retaining layer containing an organic phase capable of forming an interface with the sample containing the target ion, a first electrode to which the organic phase retaining layer is laminated and containing a first insertion material composed of an inorganic compound, a second electrode arranged so as to face the organic phase holding layer and in contact with the sample.

21 Claims, 14 Drawing Sheets

(56) References Cited

FOREIGN PATENT DOCUMENTS

| JP | 2012122883 A | * | 6/2012 |
| JP | 2018018578 A | * | 2/2018 |
| JP | 2020-052005 A | | 4/2020 |
| WO | 2021/140933 A1 | | 7/2021 |

OTHER PUBLICATIONS

Shigeo Sawada et al: "Complete Electrolysis Using a Microflow Cell with an Oil/Water Interface", Analytical Chemistry, Mar. 1, 2002, vol. 74, No. 5, pp. 1177-1181, American Chemical Society.

Asuka Yoshizumi et al: "Rapid and coulometric electrolysis for ion transfer at the aqueous|organic solution Interface", Journal of Electroanalytical Chemistry, 2005, vol. 581, pp. 275-283, Elsevier B.V.

Yumi Yoshida et al: "A flow electrolysis cell with a thin aqueous phase and a thin organic phase for the absolute determination of trace ionic species", Journal of Electroanalytical Chemistry, 2013, vol. 707, pp. 95-101, Elsevier B.V.

Shiho Tatsumi: "Development of liquid-liquid interfacial ion transfer coulometry cell using a plastic sheet as a substrate", Master's Thesis, Graduate School of Science and Technology, Kyoto Institute of Technology, Master's Program of Functional Chemistry, Submission Date: Feb. 3, 2020.

Shinichi Komaba et al., "All-solid-state ion-selective electrodes with redox-active lithium, sodium, and potassium insertion materials as the inner solid-contact layer", Analyst, Royal Society of Chemistry, UK, Oct. 21, 2017, pp. 3857-3866, vol. 142, No. 20, XP009537358. Cited in the EESR issued on Dec. 15, 2022 in the corresponding EP Application.

Extended European search report (EESR) issued on Dec. 15, 2022 in a counterpart European patent application.

* cited by examiner

ION SENSOR AND METHOD FOR MEASURING IONS

CROSS REFERENCE TO RELATED APPLICATIONS

This application claims priority from prior Japanese Patent Application(s) No. 2021-140327, filed on Aug. 30, 2021, entitled "ION SENSOR AND METHOD FOR MEASURING IONS", the entire contents of which are incorporated herein by reference.

FIELD OF THE INVENTION

The present invention relates to an ion sensor and a method for measuring ions.

BACKGROUND

Japanese Patent Application Publication No. 2012-122883 discloses an ion sensor including an organic phase retaining layer containing an organic phase capable of forming an interface with a sample containing a target ion, an electrode for an organic phase on which an organic phase retaining layer is laminated, and an aqueous phase electrode in contact with the sample, wherein the organic phase retaining layer and the aqueous phase electrode are arranged so as to face each other. In the ion sensor of Japanese Patent Application Publication No. 2012-122883, a conductive polymer film is provided between the organic phase electrode and the organic phase retaining layer in order to fix the electrode potential in the organic phase of the organic phase electrode.

In a conventional ion sensor as in Japanese Patent Application Publication No. 2012-122883, when the same sample is measured by a plurality of ion sensors, there is a possibility that the measurement results may vary among the ion sensors. Here, for example, when the ion sensor is disposable and the ion sensor is replaced each time the measurement is performed and the measurement result varies among multiple ion sensors, there is a problem in that it is difficult to distinguish whether the variation in the measurement result is due to the variation in the concentration of the ion to be measured in the sample or the variation in the measurement result between the ion sensors.

The present invention provides an ion sensor and a method for measuring ions with little variation in measurement results among a plurality of ion sensors.

SUMMARY

The ion sensor 100 (100, 200) of the present invention is a current measurement type ion sensor that measures a current to measure a target ion (31), and includes an organic phase retaining layer (13) containing an organic phase capable of forming an interface with the sample (30) containing the target ion (31), a first electrode (11) to which the organic phase retaining layer (13) is laminated and containing a first insertion material composed of an inorganic compound, a second electrode (12) arranged so as to face the organic phase holding layer (13) and in contact with the sample (30).

The method for measuring ions of the present invention used in the ion sensor (100, 200), includes a step of bringing the sample (30) into contact with the organic phase retaining layer (13) and the second electrode (12); a step of moving the target ion contained in the sample to the organic phase by applying a voltage between the first electrode (11) and the second electrode (12); and a step of measuring a current flowing between the first electrode and the second electrode.

The present invention provides an ion sensor and a method for measuring ions with little variation in measurement results among a plurality of ion sensors.

DESCRIPTION OF THE EMBODIMENTS OF THE INVENTION

Hereinafter, an example of an embodiment of the ion sensor and the ion measurement method according to the present invention will be described in detail with reference to the drawings. Note that the present invention is not limited to the embodiments and modifications described below, and the design can be appropriately changed insofar as the object of the present invention is not impaired. For example, it is within the scope of the present disclosure to selectively combine the components of the plurality of embodiments and modifications described below.

Ion Sensor Structure

Figure 1:
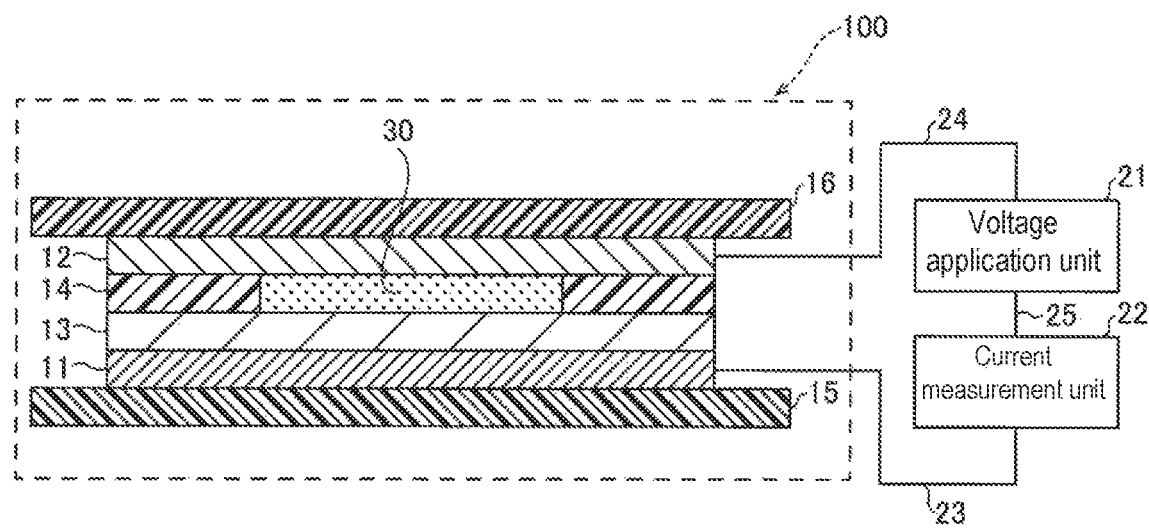
FIG. 1 is a schematic cross-sectional view showing an ion sensor.

FIG. 1 shows a schematic cross-sectional view of the ion sensor 100. As shown in FIG. 1, the ion sensor 100 is a current measurement type ion sensor that measures a current to measure target ions contained in the sample 30.

The ion sensor 100 includes a first electrode 11, a second electrode 12, an organic phase retaining layer 13, a sheet 14, an insulating substrate 15, and an insulating substrate 16. The first electrode 11 of the ion sensor 100 is connected to a current measuring unit 22 for measuring the current via a conducting wire 23. The second electrode 12 is connected to a voltage application unit 21 to which a voltage is applied via a conducting wire 24. The current measuring unit 22 includes a current measuring device. The voltage application unit 21 includes a DC power supply device in which the applied voltage is variable. The voltage application unit 21 and the current measuring unit 22 are connected to each other by a conducting wire 25.

The first electrode 11 is arranged so as to face the second electrode 12. The organic phase retaining layer 13 is laminated on the second electrode 12 side of the first electrode 11.

The first electrode 11 functions as an electrode for an organic phase. The first electrode 11 includes an electrode material and a film of an insertion material formed by applying an insertion material to the electrode material (this film is called an insertion coating film). The electrode material is formed of, for example, carbon paper. The insertion coating film may be composed of only the insertion material, or may further contain at least one of a solid electrolyte, a conductive agent and a binder.

Note that the first electrode 11 also may contain an insertion material. For example, if the insertion material itself composed of the inorganic compound contains a conductive material and the insertion material has good conductivity, the electrode material may be omitted. In this case, it is preferable to bind the insertion material with a binder and arrange it on the insulating substrate 15.

The electrode material is not particularly limited insofar as it contains a conductive material. Conductive materials include, for example, metals such as platinum, gold, silver, copper, carbon, palladium, chromium, aluminum, nickel, indium, tin, alloys containing at least one of these metals, metal halides such as chlorides of these metals, (for example, indium tin oxide) and the like. Among these, platinum, gold, silver, palladium, aluminum, nickel, carbon and the like are preferable. The conductive material may be used alone or in combination of two or more.

The content of the conductive material is, for example, 70 parts by mass or more and 100 parts by mass or less, preferably 85 parts by mass or more and 100 parts by mass or less, and more preferably 95 parts by mass or more and 100 parts by mass relative to 100 parts by mass of the electrode material.

The shape of the electrode material is not particularly limited, but is preferably flat. The layer structure of the electrode material is not particularly limited. The electrode material also may have a single-layer structure composed of one layer having a single composition, or may have a multi-layer structure composed of a plurality of layers having the same or different compositions from each other. The thickness of the electrode material is not particularly limited insofar as the conductivity is not significantly impaired. The thickness of the electrode material is, for example, 1 μm or more and 10 μm or less. From the viewpoint of manufacturing efficiency, manufacturing cost, and the like, the thickness of the electrode material is preferably 1 μm or more and 5 μm or less.

The insertion material is not particularly limited insofar as it is composed of an inorganic compound. As the insertion material, preferably, a material (ion-electron conductor) capable of inserting and removing measurement ions in the structure by an electrochemical reaction can be used. That is, the insertion material may be an ion-electron conductor. In this case, the insertion material may be an ion-electron conductor for sodium, potassium or lithium ions.

Examples of the insertion material include metal oxides, oxygen redox materials, Prussian blue analogs, and the like, and among these, metal oxides are preferable. These can be appropriately selected according to the target ion to be measured.

Examples of a metal oxide of the insertion material include $M_xMnO_2$, $M_xNiO_2$, $M_xCoO_2$, $M_xNi_{0.5}Mn_{0.5}O_2$, $M_xFeO_2$, $M_{2/3}Fe_{1/3}Mn_{2/3}O_2$, $MxNi_{1/3}Co_{1/3}Mn_{1/3}O_2$, $M_xNi_{0.5}Ti_{0.5}O_2$, $M_xVO_2$, $M_xCrO_2$, $M_xFePO_4$ (however, M is Na or K independently, and x indicates an arbitrary positive number) and the like. Among these, $M_xMnO_2$ is more preferable, and $Na_xMnO_2$ is particularly preferable.

Here, x is usually $0<x\leq1$. x is preferably 0.15 or more and 0.66 or less, more preferably 0.2 or more and 0.5 or less, and further preferably 0.22 or more and 0.28 or less, 0.30 or more and 36 or less, or 0.41 or more and 0.47 or less, and particularly preferably 0.245 or more and 0.255 or less, 0.325 or more and 0.335 or less, or 0.435 or more and 0.445 or less.

The crystal structure of the metal oxide is not particularly limited insofar as it can be used as an electrode of an ion sensor 100. Examples of the crystal structure include an orthorhombic crystal structure, a tetragonal crystal structure, a trigonal crystal structure, a hexagonal crystal structure, a cubic crystal structure, a triclinic crystal structure, a monoclinic crystal structure, and the like; and among these, an orthorhombic crystal structure is preferable.

The oxygen redox material of the insertion material is not particularly limited insofar as the material can utilize not only the transition metal but also the redox reaction of the oxide ion. Examples of an oxygen redox material include $Na_2Mn_3O_7$, $Na_{2/3}Mg_{0.28}Mn_{0.72}O_2$, $Na_2RuO_3$, $Na_{1.3}Nb_{0.3}Mn_{0.4}O_2$, and $Na_{0.6}Li_{0.2}Mn_{0.8}O_2$.

The Prussian blue analog of the insertion material is not particularly limited insofar as it has a structure in which a cyano group is crosslinked with a transition metal ion. Examples of Prussian blue analog include $Na_2Mn[Fe(CN)_6]$, $Na_yCO[Fe(CN)_6]_{0.90}\cdot2.9H_2O$ (where y indicates an arbitrary positive number), K—FeHCF (iron hexacyanoferrate potassium), K—NiHCF (nickel hexacyanoferrate potassium), K—CuHCF (copper hexacyanoferrate potassium), Na—NiHCF (nickel hexacyanoferrate) (Iron sodium), Ca—NiHCF (nickel hexacyanoferrate calcium) and the like.

Although the form of the insertion material is not particularly limited, the insertion material is preferably particles. The particles of the insertion material may have an optional shape such as scale-like, columnar, spherical, and ellipsoidal.

The average particle size of the particles of the insertion material from the viewpoint of enhancing the adhesion to the solid electrolyte and enhancing the performance of the ion sensor 100 as an electrode is preferably 1 µm or more and 20 µm or less, more preferably 2 µm or more and 15 µm or less, and even more preferably 5 µm or more and 12 µm or less. Note that the average particle size can be measured by a laser diffraction/scattering type particle size distribution measuring device.

The material and shape of the insertion material may be one type alone or a combination of two or more types.

The content of the insertion material is, for example, 20 parts by mass or more and 70 parts by mass or less, preferably 25 parts by mass or more and 65 parts by mass or less, and more preferably 30 parts by mass or more and 60 parts by mass or less relative to 100 parts by mass of the insertion coating film.

As the solid electrolyte, for example, ion conductive ceramics can be used. The ion conductive ceramics as a solid electrolyte are not particularly limited insofar as they are solids in which ions can be conducted. As the ion conductive ceramics, those capable of conducting the ion to be measured can be used.

Examples of the ion conductive ceramics include potassium ion conductive ceramics, sodium ion conductive ceramics, lithium ion conductive ceramics, calcium conductive ceramics, magnesium conductive ceramics and the like. The ion-conductive ceramics are preferably potassium ion conductive ceramics, sodium ion conductive ceramics, lithium ion conductive ceramics and the like, and particularly preferably potassium ion conductive ceramics as the ion-conductive ceramics.

The ion-conductive ceramics can be appropriately selected in accordance with the ion to be measured. Examples of ion-conductive ceramics include oxide-based solid electrolytes such as β" alumina, β-alumina, perovskite-type oxides, NASICON-type oxides, and garnet-type oxides, sulfide-based solid electrolytes, stabilized zirconia, and ion exchangers. Note that the ion exchanger is not particularly limited insofar as it is a substance exhibiting an ion exchange phenomenon, and examples include zeolites (zeolites can contain cations such as Na ion, K ion, and H ion inside), and ion exchange resin acids.

Among the ion-conductive ceramics, β" alumina, β alumina, zeolite and the like are particularly preferable from the viewpoint that the ion-conductive ceramics have high stability to water and can be suitably used as an electrode of the ion sensor 100.

β"-/β-alumina contains a layered structure consisting of an ionic conduction layer and a spinel block, and movement of ions (measurement target ions) occurs in the ionic conduction layer. β"-alumina and β-alumina are different in crystal structure, and among them, β"-alumina has a higher sodium ion content in the crystal structure and relatively higher ionic conductivity. The β"-/β-alumina is preferably Na-β"-/β-alumina capable of conducting sodium ions. Na-β" alumina usually has a chemical composition of $Na_2O \cdot xAl_2O_3$ (where x=5 or more and 7 or less). Na-β-alumina usually has a chemical composition of $Na_2O \cdot xAl_2O_3$ (where x=9 or more and 11 or less).

The form of the ion-conductive ceramics is not particularly limited, although particles are preferred. The particles of the ion-conductive ceramics as the solid electrolyte have an arbitrary shape such as a scale-like, columnar, spherical, and ellipsoidal.

The average particle size of the particles of the ion-conductive ceramics is preferably 0.02 µm or more and 7 µm or less, more preferably 0.05 µm or more and 5 µm or less, and even more preferably 0.1 µm or more and 3 µm or less, from the viewpoint of enhancing the adhesion to the insertion material and enhancing the performance of the ion sensor 100 as an electrode. Note that the average particle size can be measured by a laser diffraction/scattering type particle size distribution measuring device.

In the layer of the insertion coating film, it is preferable that the average particle size of the ion-conductive ceramics is smaller than the average particle size of the insertion material. Specifically, the ratio of the average particle diameter of the ion-conductive ceramics to the average particle diameter of the insertion material (=average diameter of the ion conductive ceramics/average diameter of the insertion material) is, for example, 0.001 or more. It is 0.3 or less, preferably 0.005 or more and 0.1 or less, and more preferably 0.01 or more and 0.05 or less. Alternatively, the ratio of the average particle size of the ion-conductive ceramics to the average particle size of the insertion material (=average particle size of the ion-conductive ceramics/average particle size of the insertion material) is, for example, 0.001 or more and 0.7 or less, preferably 0.005 or more and 0.6 or less, and more preferably 0.01 or more and 0.05 or less.

The material and shape of the ion-conducting ceramics may be one type alone or a combination of two or more types.

The content of the ion-conductive ceramics is, for example, 15 parts by mass or more and 70 parts by mass or less, preferably 20 parts by mass or more and 65 parts by mass or less, and more preferably 25 parts by mass or more and 60 parts by mass or less relative to 100 parts by mass of the insertion coating film.

The mass ratio of the insertion material to the ion-conductive ceramics in the insertion coating film (insertion material:ion-conductive ceramics) is, for example, 5:1 to 1:5, preferably 2:1 to 1:2, more preferably 1.5:1 to 1:1.5, even more preferably 1.2:1 to 1:1.2, and still more preferably 1.1:1 to 1:1.1.

Note that an ion exchange ceramic capable of performing ion exchange may be used instead of the ion-conductive ceramic or together with the ion-conductive ceramic as the solid electrolyte. The ion exchange ceramic also may be an inorganic substance such as stone, acidic clay, or palm chit, or an organic substance such as a cellulose ion exchanger or alginic acid.

The insertion coating film preferably further contains a conductive agent. In this way it is possible to improve the conductivity of the insertion coating film, improve the buffering action against volume changes due to the ingress and egress of ions, and improve the reproducibility of measurement.

The conductive agent is not particularly limited, and may be, for example, carbon materials such as carbon black, acetylene black, ketjen black, carbon nanotubes, graphene, carbon powder, and graphite powder, conductive fibers such as metal fibers, and carbon fluoride, metal powders such as aluminum, conductive whiskers such as zinc oxide and potassium titanate, conductive metal oxides such as titanium oxide, organic conductive materials such as phenylene derivatives and graphene derivatives.

The components of the conductive agent also may be used alone or in combination of two or more.

The content of the conductive agent is, for example, 0.1 part by mass or more and 20 parts by mass or less, preferably 1 part by mass or more and 15 parts by mass or less, and more preferably 2 parts by mass or more and 10 parts by mass or less relative to 100 parts by mass of the insertion coating film.

The mass ratio of the insertion material to the conductive agent (insertion material:conductive agent) in the insertion coating film is, for example, 20:1 to 1:1, preferably 15:1 to 3:1, and more preferably. It is 10:1 to 6:1.

The mass ratio of the ion-conductive ceramics to the conductive agent (ion-conductive ceramics:conductive agent) in the insertion coating film is, for example, 20:1 to 1:1, preferably 15:1 to 3:1, and more preferably 10:1 to 6:1.

The insertion coating film preferably further contains a binder. In the way each component in the insertion coating film can be bound more firmly.

The binding agent is not particularly limited, and examples of usable binding agents include polyacrylic acid vinylidene, polyvinylpyrrolidone, polytetrafluoroethylene, polyethylene, polypropylene, aramid resin, polyamide, polyimide, polyamideimide, polyacrylic nitrile, polyacrylic acid, polyacrylic acid methyl ester, polyacrylic acid ethyl ester, polyacrylic acid hexyl esters, polymethacrylic acid, polymethacrylic acid methyl ester, polymethacrylic acid ethyl ester, polymethacrylic acid hexyl ester, acrylic emulsion, polyvinyl acetate, polyvinylpyrrolidone, polyether, polyether sulfone, hexafluoropolypropylene, styrene butadiene rubber, carboxy polymers such as methylcellulose, compounds having a skeleton similar to these polymers, and composite agents consisting of multiple polymers. Among these, preferably (a) polyvinylidene fluoride, (b) a mixture containing styrene butadiene latex and carboxymethyl cellulose, (c) a mixture containing polyamide, polyimide, and carbodiimide, (d) polytetrafluoroethylene, (e) acrylic emulsion and the like, and more preferably polyvinylidene fluoride.

The component of the binder may be one kind alone or a combination of two or more kinds.

The content of the binder is, for example, 0.1 part by mass or more and 20 parts by mass or less, preferably 1 part by mass or more and 15 parts by mass or less, and more preferably 2 parts by mass or more and 10 parts by mass or less relative to 100 parts by mass of the insertion coating film.

The mass ratio of the insertion material to the binder (insertion material:binder) in the insertion coating film is, for example, 20:1 to 1:1, preferably 15:1 to 3:1, and more preferably 10:1 to 6:1.

The mass ratio of the ion-conductive ceramics to the binder (ion-conductive ceramics:binder) in the insertion coating film is, for example, 20:1 to 1:1, preferably 15:1 to 3:1, and more preferably 10:1 to 6:1.

The insertion coating film may contain components other than the above. Other components include, for example, $MnCO_3$, $Na_2CO_3$, $Al_2O_3$ and the like.

The total content of the insertion material and the ion-conductive ceramics in the insertion coating film (that is, the total content including the conductive agent and the binder, if any) is, for example, 70 parts by mass or more and 100 parts by mass or less, preferably 80 parts by mass or more and 100 parts by mass or less, more preferably 90 parts by mass or more and 100 parts by mass or less, still more preferably 95 parts by mass or more and 100 parts by mass or less, and even more preferably 99 or more and 100 parts by mass or less relative to 100 parts by mass of the insertion coating film.

In the insertion coating film, it is preferable that each component is in a mixed state.

The layer structure of the insertion coating film is not particularly limited. The insertion coating film may have a single-layer structure composed of one layer having a single composition, or may have a multi-layer structure consisting of a plurality of layers having the same or different compositions from each other.

The thickness of the insertion coating film is not particularly limited insofar as the conductivity is not significantly impaired. The thickness of the insertion coating film is, for example, 1 μm or more and 200 μm or less. From the viewpoint of production efficiency, production cost, and the like, the thickness of the insertion coating film is preferably 1 μm or more and 100 μm or less, more preferably 1 μm or more and 50 μm or less, and still more preferably 1 μm or more and 20 μm or less.

The second electrode 12 functions as an aqueous phase electrode. The second electrode 12 is arranged so as to face the organic phase retaining layer 13 and comes into contact with the sample 30. The second electrode 12 is arranged between the insulating substrate 16 and the sheet 14. Although an Ag/AgCl plate is used as the second electrode 12 (aqueous electrode) from the viewpoint that the electrode potential in the sample 30 is maintained at constant level and the electrode reactant is fixed to the electrode surface, the material used is not limited. A carbon electrode modified with a redox body, a carbon paste, platinum, gold, copper, a glass electrode and the like can also be used as a material instead of Ag/AgCl. When the sample 30 contains a constant concentration of non-measurement target ions, it is also possible to use an ion-selective electrode or the like that responds to the non-measurement target ions. The second electrode 12 also may contain a second insertion material. In this case, the second insertion material may be the same material as the first insertion material, and the second electrode 12 may be formed with the same structure as the first electrode 11. In this way the ion sensor 100 can be manufactured by using a common member for the first electrode 11 and the second electrode 12, so that the number of types of members is kept low and the mass productivity of the ion sensor 100 is improved.

The organic phase retaining layer 13 contains an organic phase capable of forming an interface with the sample 30 containing the ion to be measured. The organic phase includes an organic solvent in which an ionic substance dissolved in an aqueous solvent can move from the aqueous solvent, and a supporting electrolyte for the organic phase contained in the organic solvent.

The organic solvent should form an interface with the aqueous phase, and useful examples include a halogen-containing solvent such as dichloroethane and trichloromethane, an ether solvent such as diethyl ether and tetrahydrofuran, an aromatic solvent such as nitrobenzene and toluene, and an alkane-based solvent such as hexane. A hydrophobic ionic liquid such as asymmetric alkylammonium bis (nonafluorobutanesulfonyl) imide may be used as the organic solvent.

Supporting electrolytes for the organic phase include hydrophobic cations such as quaternary ammonium, tetraphenylphosphonium, alkylphosphonium, and imidazolium, and hydrophobic salts consisting of hydrophobic anions such as tetraphenylboric acid halide and various sulfonylimides. An ionic liquid such as an asymmetric alkylammonium halide tetraphenylborate also may be used as a substance having both a function as an organic solvent and a supporting electrolyte for an organic phase. The concentration of supporting electrolyte is $10^{-3}$ M or more and 0.1 M or less.

The organic phase is maintained by a polymer film, a porous inorganic insulator material having an affinity with the organic phase, and the like.

Examples of the polymer film include Teflon (registered trademark), polyethylene, polypropylene, polyvinyl chloride and the like, and examples of the porous inorganic insulator material include alumina and a porous film of silicon carbide. As the polymer film, the organic phase solvent may be impregnated into the polymer film prepared independently, or the organic phase solvent may be mixed with the polymer material to integrate the organic phase solvent and the polymer film. The thickness of the organic phase retaining layer 13 is not limited, and is preferably thinner from the viewpoint of back-extracting the ionic substance transferred to the organic phase into the aqueous phase. However, it is necessary to prevent the sample 30 from coming into contact with the first electrode 11 (organic phase electrode). For example, the thickness of the organic phase retaining layer 13 can be 5 μm or more and 1000 μm or less. From the perspective of manufacturing, the thickness of the organic phase retaining layer 13 is preferably 10 μm or more and 200 μm or less.

The organic phase retaining layer 13 may contain an ionophore. In this way the ion to be measured can be separated from other ions and measured with high accuracy. The ionophore is provided for selecting cations such as sodium ion and potassium ion, for example.

Ionophores include valinomycin, monesin, rhodopsin, nonactin, monactin, ionomycin, gramcidin A, nigericin, CCCP (carbonyl cyanide-m-chlorophenylhydrazone), FCCP (carbonyl cyanide-p-trifluoromethoxyphenylhydrazone), crown ether. (A group of large cyclic polyethers), and further includes acyclic nonylphenoxypolyethanol, DD16C5, Bis-12Crown-4, 12-Crown-4, 15-Crown-5, 18-Crown-6, Calex Allen and the like. The ionophore may be used alone or in combination of two or more.

Figure 2:
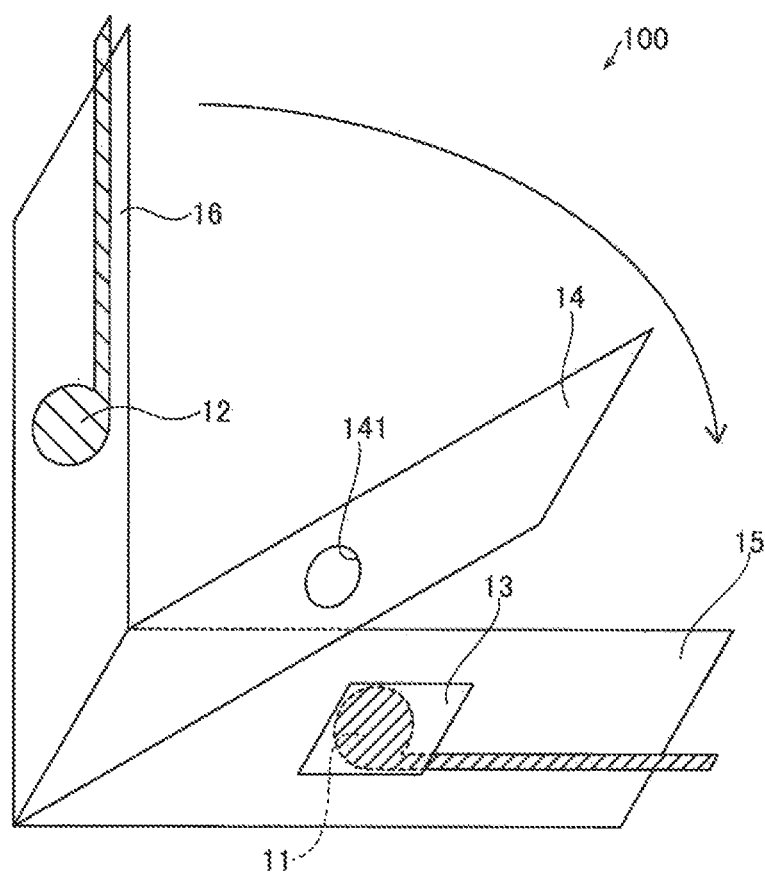
FIG. 2 is a perspective view showing an ion sensor before dropping a sample.

The sheet 14 is provided between the organic phase retaining layer 13 and the second electrode 12. The sheet 14 is formed of, for example, a thin plate made of plastic. As shown in FIG. 2, the sheet 14 a through-hole 141. As shown in FIG. 1, when the sheet 14 is sandwiched between the second electrode 12 and the organic phase retaining layer 13, a space for accommodating the sample 30 is formed by the through hole 141.

The first electrode 11 is arranged on the insulating substrate 15. The insulating substrate 15 is formed of, for example, a thin plate made of plastic.

A second electrode 12 is arranged on the insulating substrate 16. The insulating substrate 16 is formed of, for example, a thin plate made of plastic.

The insulating substrates 15 and 16 are not particularly limited insofar as they include an insulating material that does not affect the conductivity of the electrode. Examples of the insulating material include polyester resins such as polyvinyl alcohol, polyethylene terephthalate, polyethylene terephthalate, polyethylene naphtha late, and polyethylene naphtha late; fiber substrates such as polyimide, glass epoxy resin, glass, ceramics, and paper.

Here, a method of setting the sample 30 in the ion sensor 100 will be described with reference to FIGS. 2 to 4. FIG. 2 is a perspective view of the ion sensor 100 before setting the sample 30. As shown in FIG. 2, the first electrode 11 is arranged on the insulating substrate 15, and the organic phase retaining layer 13 covers the first electrode 11. A second electrode 12 is arranged on the insulating substrate 16. The insulating substrate 15, the insulating substrate 16, and the sheet 14 are rectangular sheets having the same shape as each other, and one short side thereof can be adhered to each other.

Figure 3:
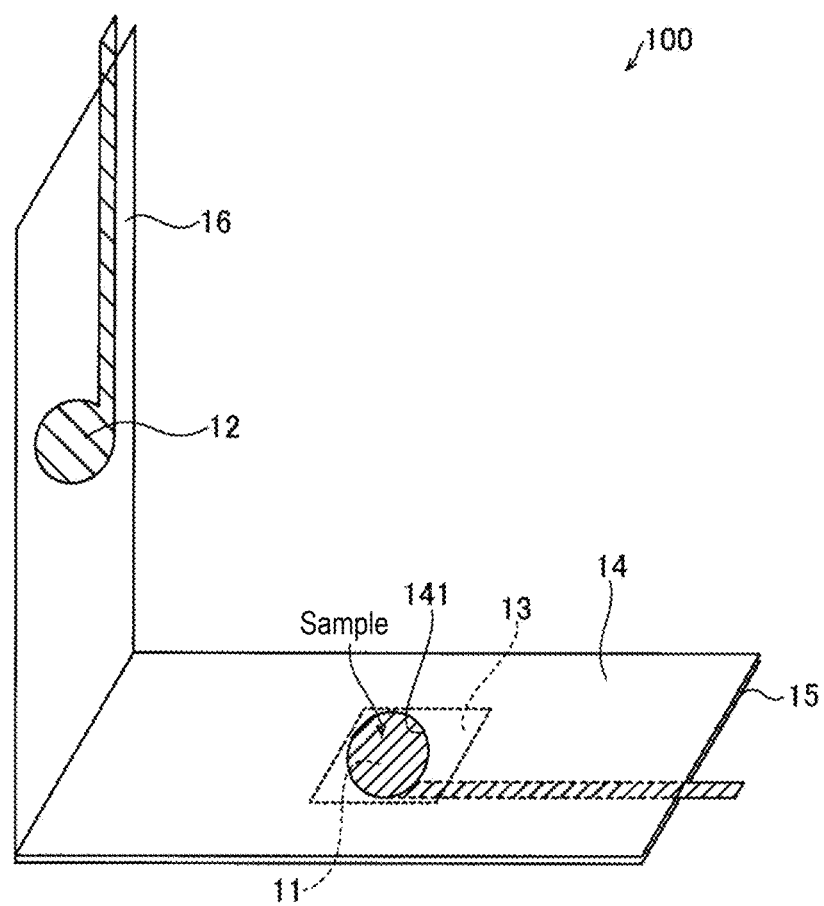
FIG. 3 is a perspective view showing an ion sensor on which a sample is dropping.
Figure 4:
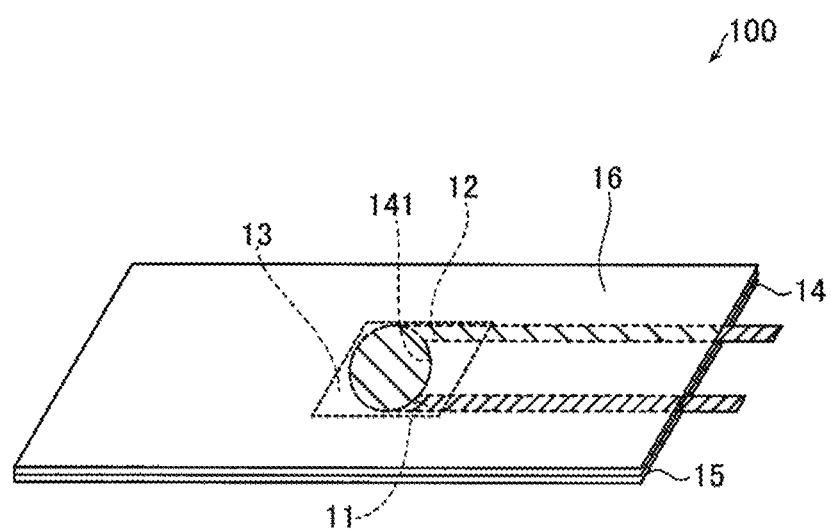
FIG. 4 is a perspective view showing an ion sensor after dropping a sample.

When the sample 30 is set in the ion sensor 100, as shown in FIG. 3, the sheet 14 is rotated to be brought into contact with the insulating substrate 15, and the sample 30 is dropped into the space formed by the through hole 141 of the sheet 14. Then, as shown in FIG. 4, the insulating substrate 16 is rotated and brought into contact with the sheet 14, and the insulating substrate 15, the insulating substrate 16, and the sheet 14 are crimped and fixed. In this way the ion sensor 100 is assembled. In the assembled ion sensor 100, the first electrode 11 is connected to the lead wire 23 (see FIG. 1), and the second electrode 12 is connected to the lead wire 24 (see FIG. 1).

The ion to be measured by the ion sensor 100 is not particularly limited, and examples thereof include potassium ion, sodium ion, lithium ion, calcium ion, and magnesium ion.

The ion sensor 100 can preferably be used as a potassium ion sensor. In hyperkalemia patients, behaviors that increase blood potassium, such as excessive intake of a high-potassium diet, can cause changes in the electrical activity of the heart to the extent that abnormalities appear on the electrocardiogram, and in some cases, fatal arrhythmias, whereas, if medication, dialysis and the like are performed while the blood potassium level is not high, it causes an excessive decrease in blood potassium, which causes paralysis and muscle spasm, and in some cases, death may occur. Since the blood potassium level varies depending on the patient's constitution, pathological condition, daily dietary content and the like, the blood potassium level should be measured by the patient himself so as not to cause an excessive decrease or increase in the blood potassium level and it is therefore desirable to be able to appropriately adjust the dose timing, dosage, meal content and such. Since the ion sensor 100 is an ion sensor in which the variation in potential between a plurality of ion sensors 100 is reduced and the need for calibration is lower (calibration-free is also possible), the ion sensor 100 is particularly suitable as a potassium ion sensor used for measurement by a hyperkalemia patient (since usually complicated and specialized work such as calibration is difficult).

The ion sensor 100 can measure a target ion by coulometry, which is one type of measurement method for detecting an electric current. Coulometry is a method of measuring the amount of substance of a target ion to be measured from the amount of electricity obtained by integrating the detected current in the range from the start of measurement to the end of measurement. Since coulometry has high measurement accuracy, it is useful in clinical examinations which require accurate detect of abnormal values that deviate from constant values such as body fluid composition. Since coulometry uses the principle of detecting a current derived from the total amount of target ions in a sample, it is a measurement method capable of absolute quantification that does not require a calibration curve, and is suitable for use in a disposable sensor.

In coulometry, the voltage applied to the ion sensor 100 can be suitably changed depending on the type of the target ion, the solvent of the sample, and the type of the organic solvent of the organic phase retaining layer, but is generally −1.5 V or more and 1.5 V or less. Specifically, it is preferable to apply the peak current potential at which the peak current can be obtained from the cyclic voltammogram as a reference. When the cations in the sample are moved and measured, it is preferable to apply a voltage to the first electrode 11 (organic phase electrode) such that the potential of the second electrode 12 (aqueous phase electrode) becomes a potential showing a positive current peak or a potential higher than that; whereas, when measuring moving anions, it is preferable to apply a voltage to the 1 electrode 11 (organic phase electrode) such that the potential of the second electrode 12 (aqueous phase electrode) becomes a potential showing a negative current peak or a potential lower than that.

In coulometry, the number of coulombs (amount of electricity) can be calculated, and the amount of substance (number of moles) of ions can be calculated from this number of coulombs by applying a voltage between the electrodes, measuring the ion transfer current accompanying the movement of cations or anions, and integrating the current from the start of measurement to the end of measurement. Note that when the ion transfer current approaches 0 A and there is no change, it can be determined that the transfer of cations or anions has been completed.

Figure 5:
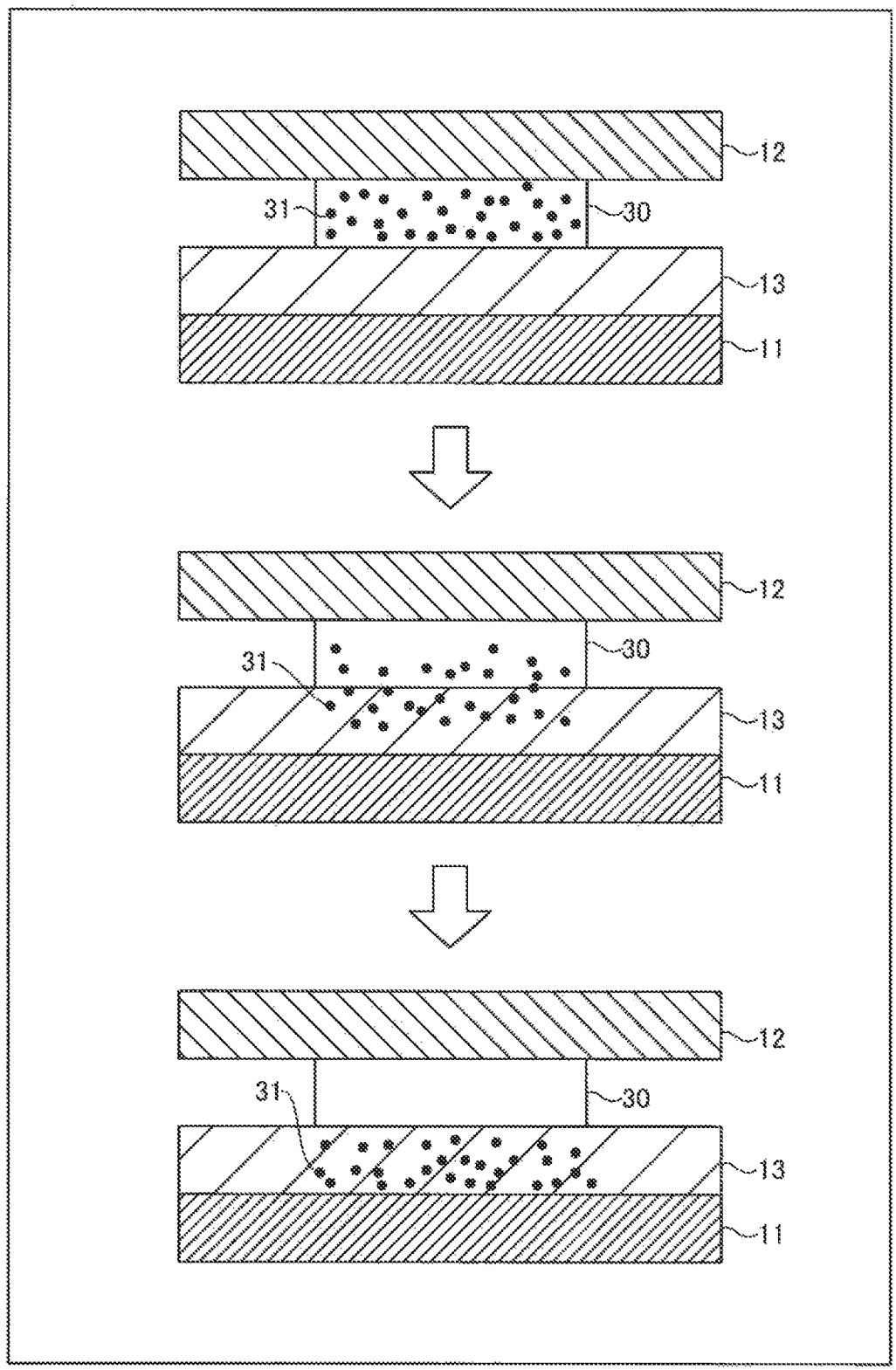
FIG. 5 is a diagram describing a method of measuring ions using an ion sensor.

Next, a method of measuring the target ion by the ion sensor 100 will be described. As shown in FIG. 5, in the ion sensor 100, the sample 30 is brought into contact with the organic phase retaining layer 13 and the second electrode 12. As a method for bringing the sample 30 into contact with the organic phase retaining layer 13 and the second electrode 12, for example, the method described with reference to FIGS. 2 to 4 can be used. Then, by applying a voltage between the first electrode 11 and the second electrode 12, the target ion 31 contained in the sample 30 is moved from the sample 30 (aqueous phase) to the organic phase retaining layer 13 (organic phase). Specifically, the target ion 31 is moved from the sample 30 (aqueous phase) to the organic phase retaining layer 13 by the voltage application unit 21 applying a constant voltage for moving the target ion 31 between the first electrode 11 and the second electrode 12 (see FIG. 1).

Due to the movement of the target ion 31, the electric charge moves and a current flows. The current flowing between the first electrode 11 and the second electrode 12 is measured by the current measuring unit 22 (see FIG. 1). Then, the amount of the target ion is obtained based on the amount of electricity (integrated current value of the sample) obtained by integrating the measured current value in the range from the start of voltage application to the end of application. Specifically, the amount of ions (mol) is determined by Q/n·F. Where Q is the measured amount of electricity (C), n is the number of charges of the target ion 31, and F is the Faraday constant (about 96485 C/mol). Q obtained by subtracting the background current integral value from the above-mentioned sample current integral value. The background current integral value is the current value obtained when the voltage applied between between the first electrode 11 and the second electrode 12 is integrated in the range from the start of the voltage application to the end of the voltage application when the target ions are not in the aqueous phase.

EXAMPLES

Examples of the ion sensor 100 of this embodiment will be described below.

Example 1

In Example 1, the first electrode 11 (the electrode for the organic phase) was fabricated by applying a paste of a metal oxide ($Na_{0.33}MnO_2$ (orthorhombic crystal structure), average particle size 7.3 μm, flaky), a solid electrolyte (β"-alumina: $Na_2Al_{10.6}O_{15.9}$, average particle size 0.99 μm), a conductive material (acetylene black), and a binder (polyvinylidene fluoride) to a carbon paper using a squeegee to form an insertion coating film.

An Ag/AgCl electrode was used as the second electrode 12 (aqueous phase electrode).

The organic phase retaining layer 13 was prepared by impregnating a Teflon porous membrane (thickness: 30 μm) with nitrophenyl octyl ether (NPOE), which is an organic solvent with added 0.01 M BTPPATFBP as a supporting electrolyte.

In the ion sensor 100 of Example 1, the organic phase retaining layer 13 is laminated on the insertion coating film of the first electrode 11, and a sheet 14 (thickness: 100 μm) provided with a through-hole 141 having a diameter of 5 mm for holding a sample was laminated thereon. Then, 1 μL of the sample was dropped into the through-hole 141 of the sheet 14 with a micropipette, and then the second electrode 12 was covered. Three cells assembled by crimping and fixing the first electrode 11, the organic phase retaining layer 13, the sheet 14 containing the sample, and the second electrode 12 were prepared and used for the measurement.

Example 2

In Example 2, the first electrode 11 (electrode for the organic phase) was produced by applying a paste containing a metal oxide ($Na_{0.33}MnO_2$ (orthorhombic crystal structure), average particle size 7.3 μm, flaky) as an insertion material, a conductive material (acetylene black), and binder (polyvinylidene fluoride) on carbon paper using a squeegee to form an insertion coating film. That is, the first electrode 11 of Example 2 does not contain a solid electrolyte (β"-alumina) as compared with Example 1. Note that other aspects the Example 2 are the same as those of Example 1.

Example 3

In Example 3, the first electrode 11 (the electrode for the organic phase) was fabricated by electrostatically applying a paste of a metal oxide ($Na_{0.33}MnO_2$ (orthorhombic crystal structure), average particle size 7.3 μm, flaky), a solid electrolyte (β"-alumina: $Na_2Al_{10.6}O_{15.9}$, average particle size 0.99 μm), a conductive material (acetylene black), and a binder (polyvinylidene fluoride) to a carbon paper to form an insertion coating film. That is, the first electrode 11 of Example 3 differs in that it is formed by electrostatically applying an insertion coating film to Example 1. Note that other aspects the Example 3 are the same as those of Example 1.

Example 4

In Example 4, ionophore (0.01M valinomycin) was further added to the organic phase retaining layer 13 of Example 1. Note that other aspects the Example 4 are the same as those of Example 3.

Example 5

In Example 5, the first electrode 11 (the electrode for the aqueous phase) was fabricated by applying a paste of a metal oxide ($Na_{0.33}MnO_2$ (orthorhombic crystal structure), average particle size 7.3 μm, flaky), a solid electrolyte (β"-alumina: $Na_2Al_{10.6}O_{15.9}$, average particle size 0.99 μm), a conductive material (acetylene black), and a binder (polyvinylidene fluoride) to a carbon paper using a squeegee to form an insertion coating film. That is, in Example 5, the first electrode 11 and the second electrode 12 have the same structure. Note that other aspects Example 5 are the same as those of Example 4.

Example 6

In Example 6, the first electrode 11 and the second electrode 12 have the same structure as that of Example 2, but ionophore (0.01M valinomycin) was further added to the organic phase retaining layer 13. Note that other aspects of Example 6 are the same as those of Example 2.

Comparative Example

In the Comparative Example, the first electrode (electrode for the organic phase) was prepared by applying PEDOT-PEG: TFBP-dispersed methanol solution (3 g/L) to carbon paper and drying it to form a coating film. Note that other aspects of the Comparative Example are the same as those of Example 1.

Table 1 below summarizes the configurations of the ion sensors of Examples 1 to 6 and the Comparative Example.

FIG. 1), and the applied voltage value is gradually changed by 20 mV per second in the positive direction to a predetermined positive voltage value, and after reaching the predetermined positive voltage value, the applied voltage value is gradually changed by 20 mV per second in the negative direction to the above-mentioned predetermined negative voltage value. Note that the case where the potential of the second electrode 12 is high is regarded as a positive voltage value with respect to the potential of the first electrode 11, and the case where the potential of the second electrode 12 is low is regarded as a negative voltage value. The current value at each voltage value was measured by the current measuring unit 22 (see FIG. 1), and a cyclic voltammogram (current/voltage characteristic waveform; hereinafter referred to as voltammogram) was created based on the measured current value.

In Measurement Example 1, the ion sensor of Example 1, the ion sensor of Example 2, the ion sensor of Example 3, and the ion sensor of the Comparative Example were used to measure using three cells (Cell 1 to Cell 3), and a voltammogram was created for each cell.

Figure 6:
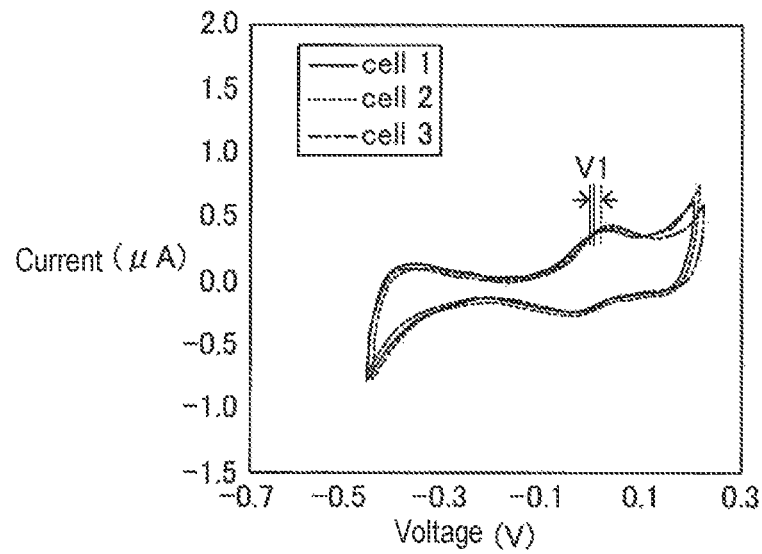
FIG. 6 is a voltammogram showing the results of current measurement performed by the ion sensor of Example 1 in Measurement Example 1.
Figure 7:
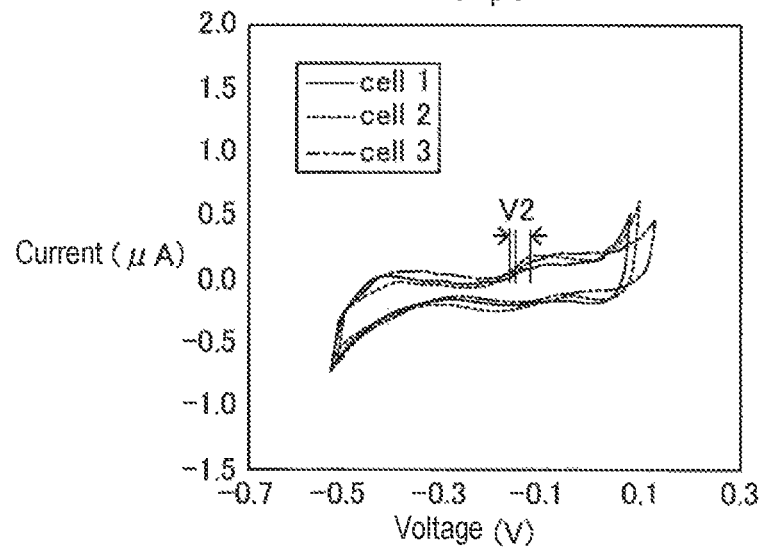
FIG. 7 is a voltammogram showing the results of current measurement performed by the ion sensor of Example 2 in Measurement Example 1.
Figure 8:
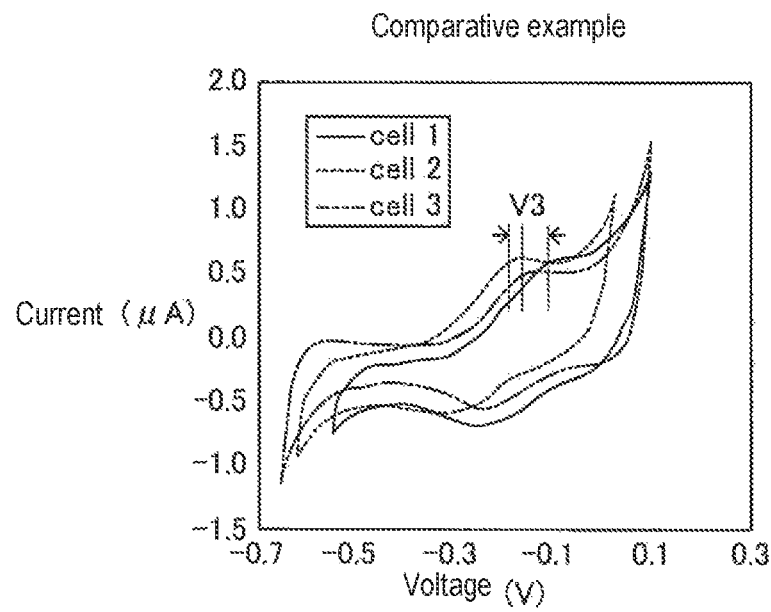
FIG. 8 is a voltammogram showing the result of measuring the current with the ion sensor of the Comparative Example in the Measurement Example 1.

FIG. 6 is a voltammogram using the ion sensor of Example 1, FIG. 7 is a voltammogram using the ion sensor of Example 2, and FIG. 8 is a voltammogram using the ion

TABLE 1

|  | 1$^{st}$ Electrode (Organic phase electrode) | Organic phase retaining layer | 2$^{nd}$ Electrode (Aqueous phase electrode) |
|---|---|---|---|
| Example 1 | Carbon Paper/ Insertion material (Na$_{0.33}$MnO$_2$) β'-alumina paste coating | Nitrophenyl octyl ether 0.01M BTPPATFPB Porous Teflon | Ag/AgCl |
| Example 2 | Carbon Paper/ Insertion material (Na$_{0.33}$MnO$_2$) Paste coating | Same as Example 1 | Same as Example 1 |
| Example 3 | Carbon Paper/ Insertion material (Na$_{0.33}$MnO$_2$) β'-alumina electrostatic coating | Same as Example 1 | Same as Example 1 |
| Example 4 | Same as Example 3 | Nitrophenyl octyl ether 0.01M BTPPATFPB Porous Teflon 0.01M Valinomycin | Same as Example 1 |
| Example 5 | Same as Example 3 | Same as Example 4 | Carbon Paper/ Insertion material (Na$_{0.33}$MnO$_2$) β'-alumina paste coating |
| Example 6 | Same as Example 2 | Same as Example 4 | Same as Example 2 |
| Comparative Ex. | Carbon Paper/ PEDOT-PEG:TFPB | Same as Example 1 | Same as Example 1 |

Measurement Example 1

Measurement Example 1 was performed using the ion sensors of Examples 1 to 3 in order to evaluate the reproducibility of the measured values among the plurality of ion sensors, that is, the magnitude of the variation. As Measurement Example 1, the cations contained in the sample were measured using the ion sensors of Examples 1 to 3 and the Comparative Example. In Measurement Example 1, an aqueous solution containing $10^{-4}$ M of tetraethylammonium chloride containing tetraethylammonium ion (TEA), which is the target ion for measurement, and 0.01M of supporting electrolyte NaCl was used as a sample.

Figure 9:
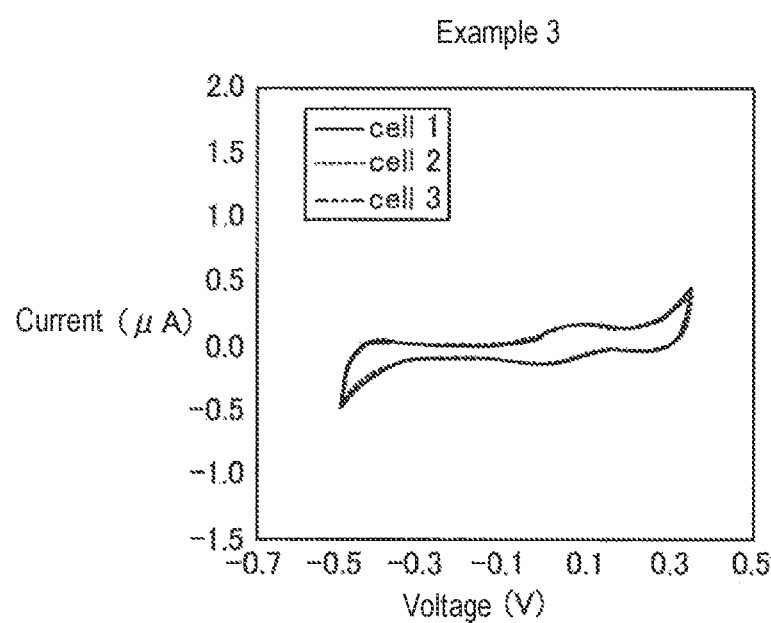
FIG. 9 is a voltammogram showing the results of current measurement performed by the ion sensor of Example 3 in Measurement Example 1.

In Measurement Example 1, a predetermined negative voltage is applied between the first electrode 11 and the second electrode 12 by the voltage application unit 21 (see sensor of the comparative example, and FIG. 9 is a voltammogram using the ion sensor of Example 3. Comparing the voltammograms using the ion sensors of Examples 1 to 3 with the voltammogram using the ion sensor of the comparative example, the voltammograms of Examples 1 to 3 have almost overlapping voltammograms of the three cells (Cell 1 to Cell 3), whereas the voltammograms of the Comparative Example of the three cells (Cell 1 to Cell 3) do not overlap. Therefore, it can be seen that the ion sensors of Examples 1 to 3 have less variation in the measured values among the plurality of ion sensors than the ion sensors of the comparative example.

In the voltammograms, the voltage value indicating the current peak corresponding to the target ion is the voltage value that moves the target ion most efficiently, and the variation of the current peak among the plurality of ion sensors is small, and the variation of the measured value of the target ion among a plurality of ion sensors also is small. As shown in FIG. 6, in the ion sensor of Example 1, the variation between cells of the voltage value at the peak of the positive current is V1. As shown in FIG. 7, in the ion sensor of Example 2, the variation between the cells of the voltage value at the peak of the positive current is V2. As shown in FIG. 8, in the ion sensor of the comparative example, the variation between cells of the voltage value at the peak of the positive current is V3. As shown in FIGS. 6 to 8, the variation of the voltage value between cells is V1<V2<V3. When the ion sensor of Example 1 and the ion sensor of Comparative Example are compared, the variation of the voltage value between the cells of the ion sensor of Example 1 is smaller and, therefore, it can be seen that the variation in the measured values among the plurality of ion sensors is smaller than that of the ion sensor in the comparative example. Similarly, when the ion sensor of Example 2 and the ion sensor of Comparative Example are compared, the variation of the voltage value between the cells of the ion sensor of Example 2 is smaller and, therefore, it can be seen that the variation in the measured values among the plurality of sensors is smaller than that of the Comparative Example.

When the ion sensor of Example 1 and the ion sensor of Example 2 are compared, the variation of the voltage value between the cells of the ion sensor of Example 1 is smaller and, therefore, it can be seen that the variation in the measured values among the plurality of ion sensors is smaller than that of the ion sensor in Example 2. From this, it can be seen that by incorporating the solid electrolyte (β"-alumina) in the first electrode 11, the variation in the measured values among the plurality of ion sensors can be further reduced.

Measurement Example 2

Measurement Example 2 was performed to evaluate the effect of change over time on the ion sensor of Example 3. As in Measurement Example 1, an aqueous solution containing $10^{-4}$ M tetraethylammonium chloride containing TEA ion, which is a target ion, and 0.01M of supporting electrolyte NaCl was used. In Measurement Example 2, the same cell was subjected to current measurement in the same manner as in Measurement Example 1 on the 1st, 2nd, 3rd, 5th, and 7th days after assembly to prepare a voltammogram.

Figure 10:
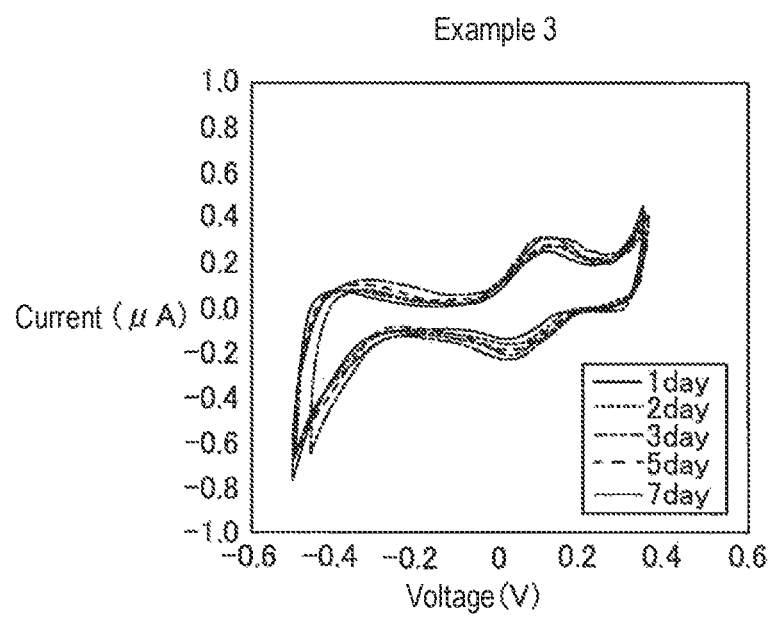
FIG. 10 is a voltammogram showing the results of current measurement performed by the ion sensor of Example 3 in Measurement Example 2.
Figure 11:
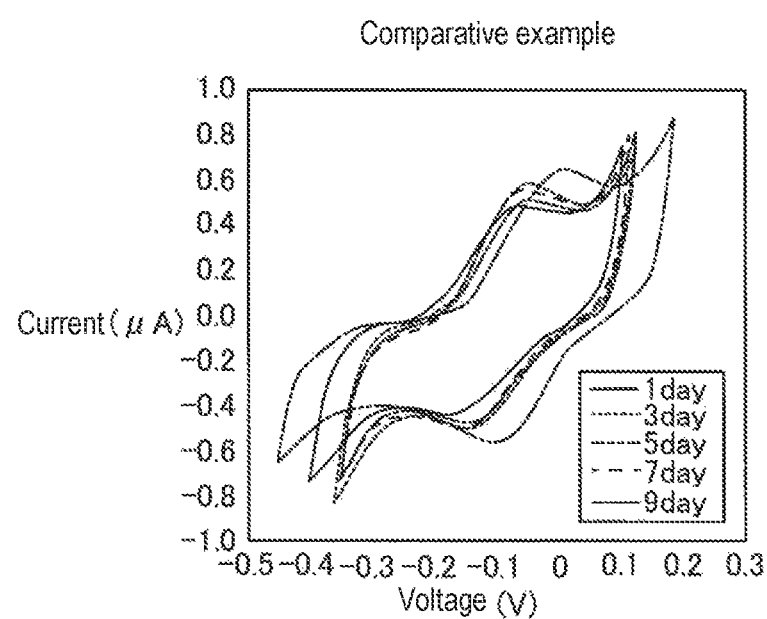
FIG. 11 is a voltammogram showing the result of measuring the current with the ion sensor of the Comparative Example in the Measurement Example 2.

FIG. 10 is a voltammogram using the ion sensor of Example 3, and FIG. 11 is a voltammogram using the ion sensor of the Comparative Example. In the ion sensor of Example 3, the measurement was performed on the 1st day, the 2nd day, the 3rd day, the 5th day and the 7th day. In the ion sensor of the Comparative Example, the measurement was performed on the 1st day, the 3rd day, the 5th day, the 7th day and the 9th day. Note that in Measurement Example 2, since the measurement is performed multiple times using the same cell, all the target ions are moved from the organic phase to the aqueous phase (sample) (reverse extraction) after each measurement, and no target ions remain in the organic phase, and after that, the electrodes were stored in a dry state with the sample removed.

When comparing Example 3 and Comparative Example, in the ion sensor of Example 3 shown in FIG. 10, the voltammogram is plotted at almost the same position for each measurement, whereas the voltammogram of Comparative Example shown in FIG. 11 is plotted at different positions depending on the measurement date. Therefore, it can be seen that the ion sensor of Example 3 has better reproducibility than the ion sensor of the Comparative Example even after a lapse of time.

Measurement Example 3

Measurement Example 3 was performed to evaluate the effect of repeated measurements of anions on the ion sensors of Examples 1 and 2. As Measurement Example 3, the anions contained in the sample were measured using the ion sensors of Examples 1 and 2 and the Comparative Example. In Measurement Example 3, an aqueous solution of 10 mM NaCl, as a supporting electrolyte, and 0.1 mM Na picrinate, a salt of the picrinate ion to be measured, was used as the sample. Also as a sample in the comparative example, an aqueous solution of 10 mM $MgCl_2$, as a supporting electrolyte, and 0.1 mM of sodium picric acid, a salt of the picric acid ion to be measured, was used. In Measurement Example 3, the ion sensor of Example 1, the ion sensor of Example 2, and the ion sensor of the Comparative Example are used one by one, and the change of the applied voltage value from the predetermined negative voltage value to the predetermined positive voltage value and returning to the predetermined negative voltage value is repeated 3 to 4 times, and the current is measured at each voltage value to create a voltammogram similar to Measurement Example 1.

Figure 12:
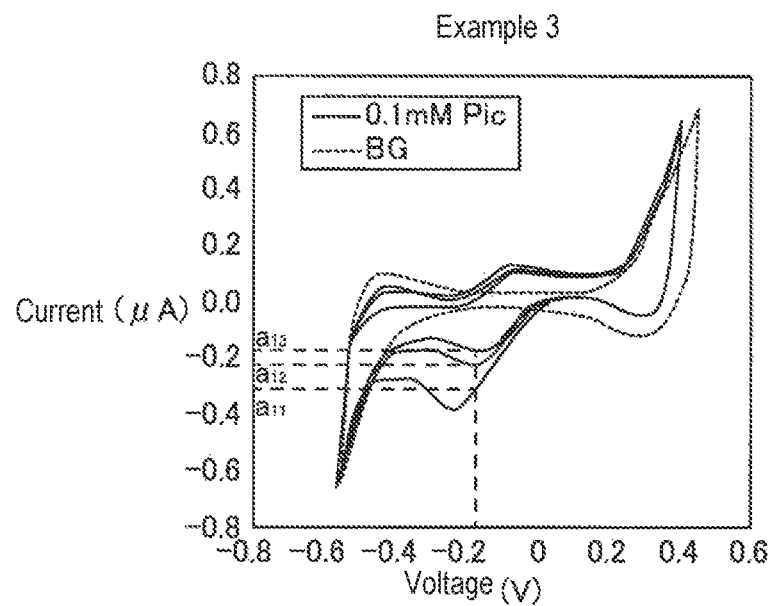
FIG. 12 is a voltammogram showing the results of current measurement performed by the ion sensor of Example 3 in Measurement Example 3.
Figure 13:
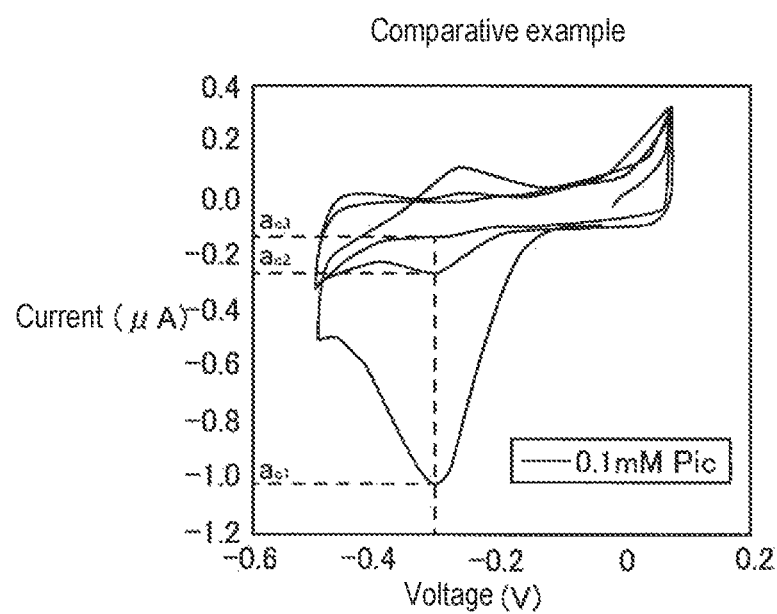
FIG. 13 is a voltammogram showing the result of measuring the current with the ion sensor of the Comparative Example in the Measurement Example 3.
Figure 14:
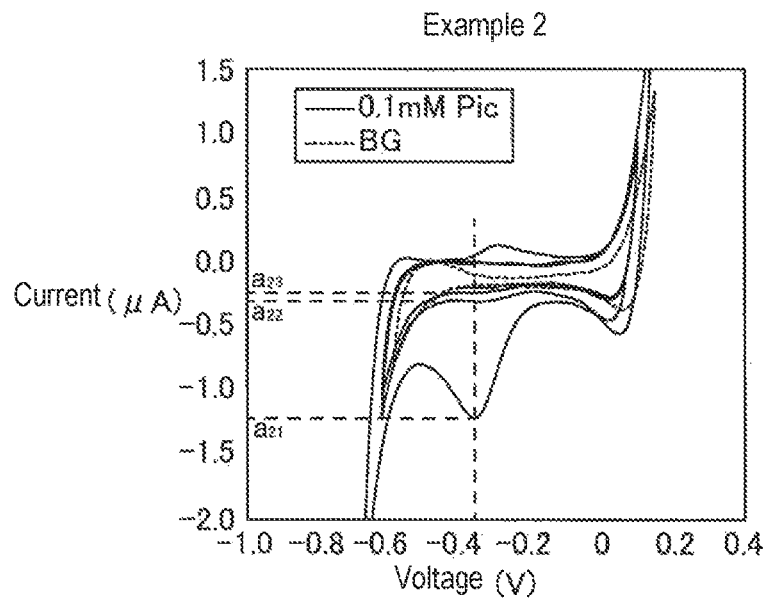
FIG. 14 is a voltammogram showing the results of current measurement performed by the ion sensor of Example 2 in Measurement Example 3.

FIG. 12 is a voltammogram using the ion sensor of Example 3, FIG. 13 is a voltammogram using the ion sensor of the Comparative Example, and FIG. 14 is a voltammogram using the ion sensor of Example 2.

In the ion sensor of Example 3, the current peak for picric acid ion was when the applied voltage was −0.15 V. In FIG. 12, the current value $a_{11}$ indicates the current value when a voltage of −0.15 V is applied for the first time, and the current value $a_{12}$ indicates the current value when a voltage of −0.15 V is applied for the second time, and the current value $a_{13}$ indicates the current value when a voltage of −0.15 V is applied for the third time.

In the ion sensor of the Comparative Example, the current peak for picric acid ion occurred when the applied voltage was −0.3 V. In FIG. 13, the current value $a_{c1}$ indicates the current value when a voltage of −0.3 V is applied for the first time, and the current value $a_{c2}$ indicates the current value when a voltage of −0.3 V is applied for the second time, and the current value $a_{c3}$ indicates the current value when a voltage of −0.3 V is applied for the third time. Comparing Example 3 and the Comparative Example, while the change from the current value $a_{11}$ to the current value $a_{13}$ is small in the ion sensor of Example 3, the change of the current value $a_{c1}$ to the current value $a_{c3}$ is large in the ion sensor of the Comparative Example. Therefore, it can be seen that the ion sensor of Example 3 is less affected by repeated measurements than the ion sensor of the Comparative Example.

In the ion sensor of Example 2, the current peak for picric acid ion occurred when the applied voltage was −0.35 V. In FIG. 14, the current value $a_{21}$ indicates the current value when a voltage of −0.35 V is applied for the first time, and the current value $a_{22}$ indicates the current value when a voltage of −0.35 V is applied for the second time, and the current value $a_{23}$ indicates the current value when a voltage of −0.35 V is applied for the third time. Comparing Example 2 and the Comparative Example, while the change from the current value $a_{21}$ to the current value $a_{23}$ is small in the ion sensor of Example 2, the change from the current value $a_{c1}$ to the current value $a_{c3}$ is large in the ion sensor of the Comparative Example. Therefore, it can be seen that the ion sensor of Example 2 is less affected by repeated measurements than the ion sensor of the Comparative Example. On the other hand, comparing Example 2 and Example 1, while the change from the current value $a_{21}$ to the current value $a_{23}$ is large in the ion sensor of Example 2, the change from the current value $a_{11}$ to the current value $a_{13}$ is small in the ion sensor of Example 1. Therefore, it can be seen that the ion sensor of Example 1 is less affected by repeated measurements than the ion sensor of the Example 2. That is, in Example 1 in which the first electrode 11 contains a solid electrolyte (β"-alumina), it can be seen that the influence of repeated measurements is further suppressed compared to Example 2 in which the first electrode 11 does not contain a solid electrolyte (β"-alumina). From this, it can be said that it is preferable that the first electrode 11 contains a solid electrolyte (β"-alumina) when the anion measurement is repeatedly performed.

Measurement Example 4

Measurement Example 4 was performed to evaluate the effect of repeated measurement of cations on the ion sensor of Example 4. In Measurement Example 4, an aqueous solution containing 14 mM NaCl containing Na ion, which is the ion to be measured, was used as a sample. In Measurement Example 4, one ion sensor of Example 4 was used, and as in Measurement Example 1, an applied voltage that changes from a predetermined negative voltage value to a predetermined positive voltage value and returns to a predetermined negative voltage value was repeated three to four times, the current was measured at each voltage value, and a voltammogram was created.

Figure 15:
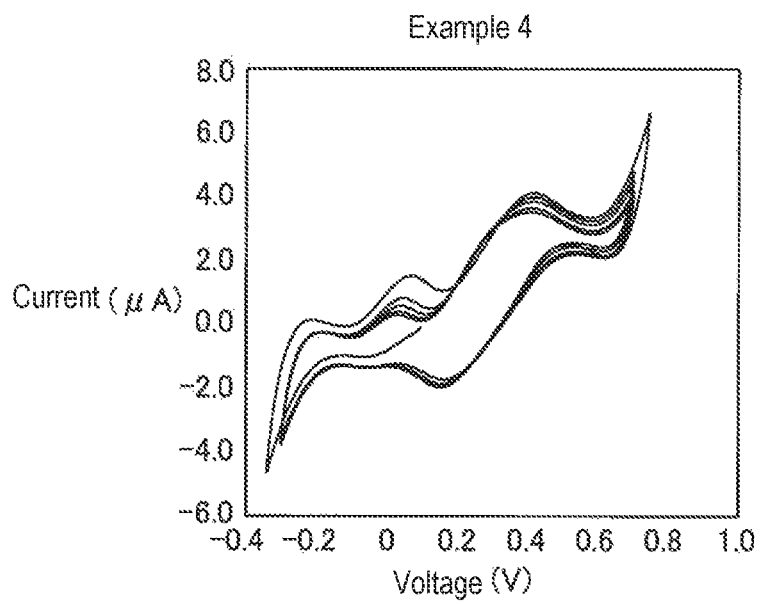
FIG. 15 is a voltammogram showing the results of current measurement performed by the ion sensor of Example 4 in Measurement Example 4.

FIG. 15 is a voltammogram using the ion sensor of Example 4.

In the ion sensor of Example 4, the current peak for Na ions occurred when the applied voltage was 0.4 V. In FIG. 15, the current value when the applied voltage is 0.4 V scarcely changes between the first measurement and the third measurement. Therefore, in the ion sensor of Example 4, it can be seen that the Na ions that have moved from the sample, which is in the aqueous phase, to the organic phase return from the organic phase to the aqueous phase. In the ion sensor of Example 4, it also can be seen that valinomycin, which is an ionophore, does not affect the repeated measurement of Na ions. Therefore, it can be seen that the ion sensor of Example 4 can repeatedly measure Na ions.

Measurement Example 5

Measurement Example 5 was performed to evaluate the possibility of measuring a sample containing two types of cations with respect to the ion sensors of Example 4 and Example 5. In Measurement Example 5, an aqueous solution containing 14 mM NaCl and 1.0 mM KCl was used as as a first sample containing the target ions Na ion and K ion, an aqueous solution of 14 mM NaCl and 0.4 mM KCl was used as a second sample containing the target ions Na ions and KCl ions, and an aqueous solution containing 14 mM NaCl was used as a third sample containing Na ion as a measurement target ion. In Measurement Example 5, the ion sensors of Example 4 and Example 5 are used one by one, and the current is measured for each of the first sample and the second sample while changing the voltage value in the same manner as in Measurement Example 1 to create a voltammogram.

Figure 16:
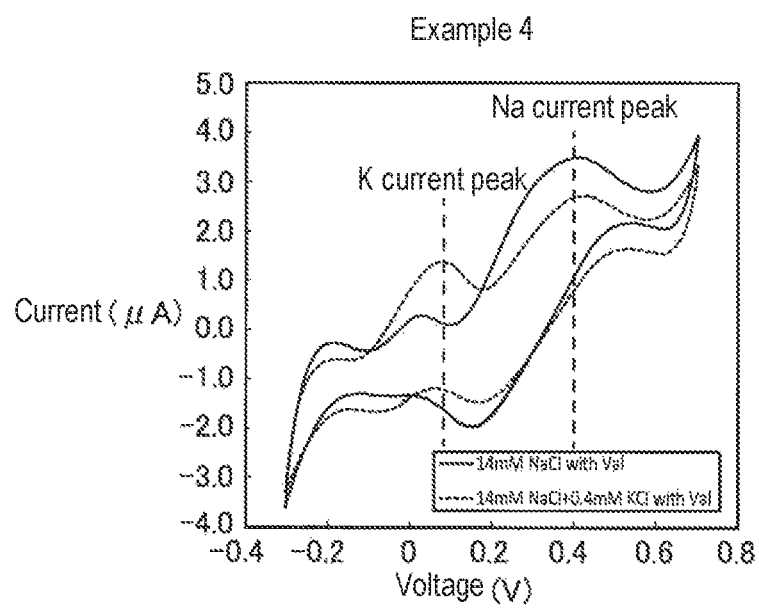
FIG. 16 is a voltammogram showing the results of current measurement performed by the ion sensor of Example 4 in Measurement Example 5.
Figure 17:
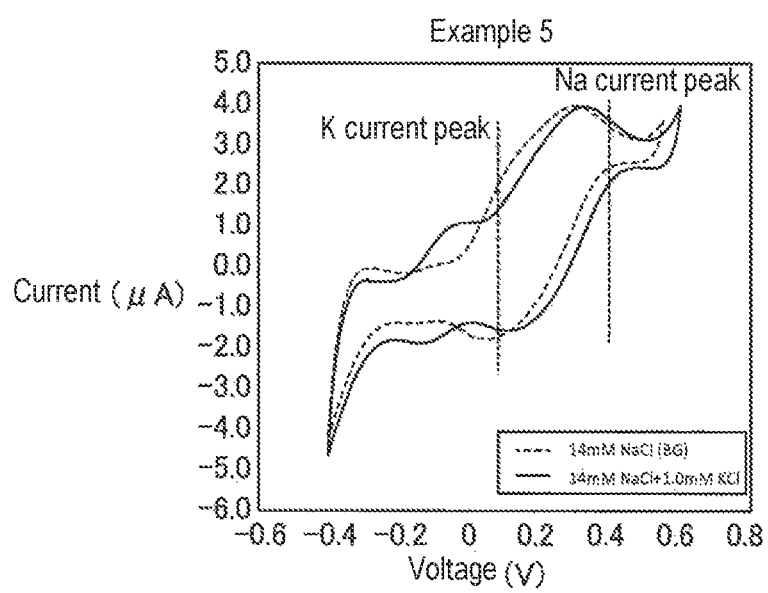
FIG. 17 is a voltammogram showing the results of current measurement performed by the ion sensor of Example 5 in Measurement Example 5.

FIG. 16 is a voltammogram using the ion sensor of Example 4. FIG. 14 is a voltammogram using the ion sensor of Example 5.

In the ion sensor of Example 4, it was noted as a result of measuring the first sample, the current peak for Na ion was when the applied voltage was 0.4V. In the ion sensor of Example 4, it was noted as a result of measuring the third sample, the current peak for Na ion was when the applied voltage was 0.4V. In the ion sensor of Example 4, the current peaks for Na ions were the same in the first sample and the third sample. In the ion sensor of Example 4, as a result of measuring the first sample, the current peak for K ions could be detected when the applied voltage was 0.1 V.

From this, it can be seen that the ion sensor of Example 4 can measure the target ion even in a sample containing a plurality of types of ions.

In the ion sensor of Example 5, as a result of measuring the second sample, the current peak for the sodium ion occurred when the applied voltage was 0.3 V. In the ion sensor of Example 5, as a result of measuring the third sample, the current peak for the sodium ion was detected when the applied voltage was 0.3 V. In the ion sensor of Example 5, the current peaks for Na ions were the same in the second sample and the third sample. In the ion sensor of Example 5, as a result of measuring the second sample, the current peak for K ion could be detected when the applied voltage was 0 V. From this, it can be seen that the ion sensor of Example 5 can measure the target ion even in a sample containing a plurality of types of ions. Further, in the ion sensor of Example 5, it can be seen that Na ion and K ion can be measured even if the second electrode 12 (see FIG. 1), which is the aqueous phase side electrode, contains an insertion material.

Measurement Example 6

Measurement Example 6 was performed to evaluate the accuracy of the amount of electricity (the above-mentioned amount of electricity Q) measured by coulometry with respect to the ion sensors of Examples 4 and 6. In Measurement Example 6 using the ion sensor of Example 4, an aqueous solution containing 0.2 mM of KCl, an aqueous solution containing 0.4 mM of KCl, and an aqueous solution containing 0.8 mM of KCl were used as samples containing K ion which is a measurement target ion. Each aqueous solution also contained 14 mM NaCl as a supporting electrolyte. One ion sensor of Example 4 was used for each concentration, 0.1 V, which is the voltage at which the peak current of K ions was generated, was applied, the current was measured, and the electric energy Q was calculated by the above-mentioned method. The measurement was performed 5 times for one concentration, and the average and standard deviation of the electric energy Q calculated for each measurement were obtained. In addition, the theoretical electric energy was calculated for each aqueous solution, and the electrolytic efficiency was calculated from the theoretical electric energy and the average and standard deviation of the electric energy Q calculated for each measurement.

The results are shown in Table 2 below.

TABLE 2

| KCl Concentration (mM) | Theoretical electric energy (μC) | Electric energy Q (μC) | Electrolysis efficiency (%) |
| --- | --- | --- | --- |
| 0.2 | 19.1 | 20 ± 1 | 104 ± 6 |
| 0.4 | 38.2 | 40 ± 2 | 103 ± 6 |
| 0.8 | 76.4 | 84 ± 2 | 110 ± 2 |

From this result, it can be seen that the electrolysis efficiency is close to 100%, and the ion sensor of Example 4 can measure K ions with high accuracy.

In Measurement Example 6 using the ion sensor of Example 6, an aqueous solution containing 0.4 mM KCl and an aqueous solution containing 0.8 mM KCl were used as samples containing K ion, which is a measurement target ion. Each aqueous solution also contained 14 mM NaCl as a supporting electrolyte. Two ion sensors (cells) of Example 6 were used for each concentration, 0.1 V, a voltage at which the peak current of K ions is generated, was applied, the current was measured, and the amount of electricity Q was calculated by the above method. The measurement was performed once for each cell for each concentration (twice in total), and the electric energy Q was calculated for each measurement. The theoretical electric energy was calculated for each aqueous solution, and the electrolytic efficiency was calculated from the theoretical electric energy and the electric energy Q calculated for each measurement.

The results are shown in Tables 3 and 4 below. Table 3 shows the results of the 0.4 mM KCl solution, and Table 4 shows the results of the 0.8 mM KCl solution.

TABLE 3

|  | Theoretical electric energy (μC) | Electric energy Q (μC) | Electrolysis efficiency (%) |
| --- | --- | --- | --- |
| Cell 1 | 38.2 | 32.6 | 85 |
| Cell 2 | 38.2 | 39.3 | 103 |

TABLE 4

|  | Theoretical electric energy (μC) | Electric energy Q (μC) | Electrolysis efficiency (%) |
| --- | --- | --- | --- |
| Cell 3 | 76.4 | 77.8 | 102 |
| Cell 4 | 76.4 | 84.7 | 111 |

From this result, it can be seen that the electrolysis efficiency is close to 100%, and the ion sensor of Example 6 can measure K ions with high accuracy. Therefore, it can be seen that the coulometry measurement is possible even if the first electrode 11 does not contain the solid electrolyte (β"-alumina).

Modifications

It should be noted that the embodiments (and examples) disclosed herein should be considered exemplary in all respects and not restrictive. [fuzzy] The scope of the present invention is indicated not by the description of the above embodiments but by the scope of the claims, and includes meanings equivalent to the claims and all changes within the scope thereof.

In the above embodiment, an example of the ion sensor 100 having a structure in which the sample is dripped into the through hole 141 of the sheet 14 and then covered with the second electrode 12 is shown, but the present invention is not limited to this. As shown in FIGS. 18 to 25, the ion sensor 200 of the modified example is configured to supply the sample 30 between the second electrode 12 and the organic phase retaining layer 13 in a state in which the first electrode 11 and the second electrode 12 are arranged so as to face each other. In this case, the sample 30 may be suctioned into the space between the second electrode 12 and the organic phase retaining layer 13 from the side of the ion sensor by capillary force.

Figure 18:
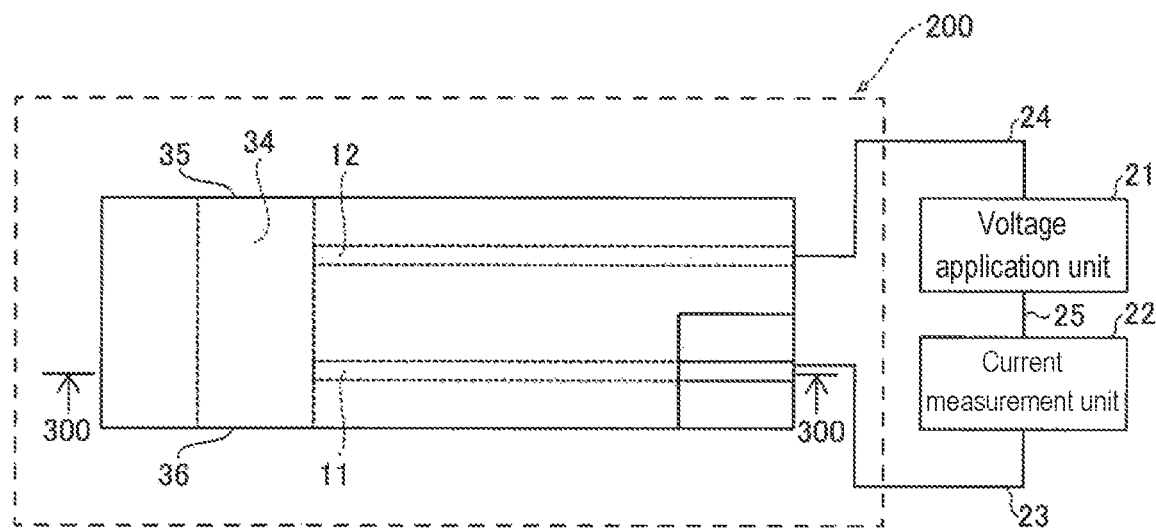
FIG. 18 is a plan view showing an ion sensor according to a modified example.
Figure 19:
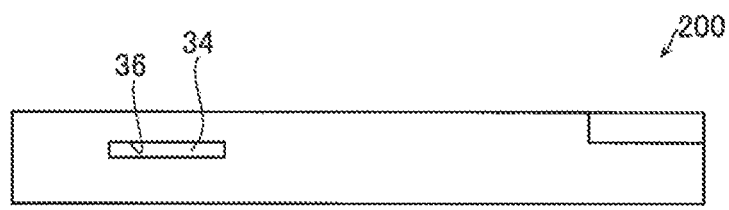
FIG. 19 is a schematic side view showing an ion sensor according to a modified example.
Figure 20:
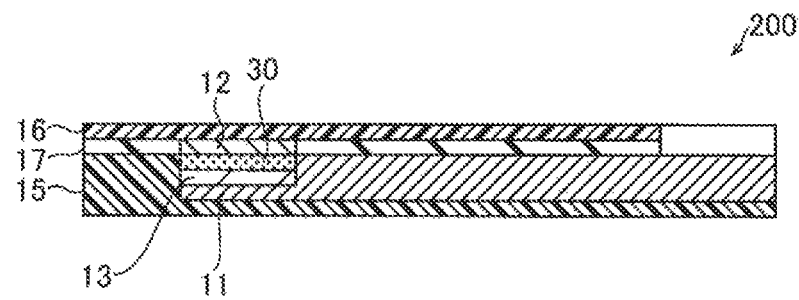
FIG. 20 is a schematic cross-sectional view along the line 300-300 of FIG. 18.
Figure 21:
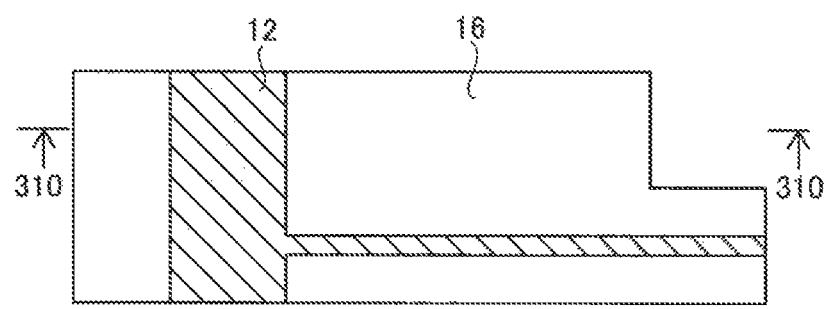
FIG. 21 is a bottom view showing an insulating substrate on which a second electrode is laminated.
Figure 22:
FIG. 22 is a schematic cross-sectional view along the line 310-310 of FIG. 21.
Figure 23:
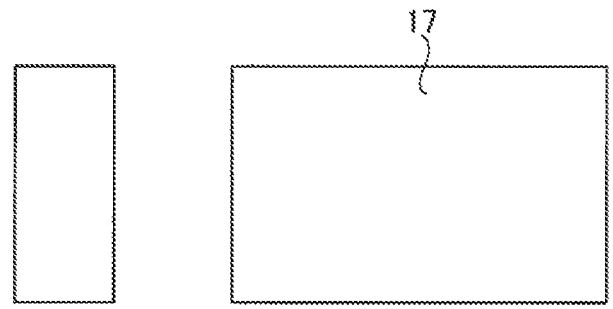
FIG. 23 is a plan view showing an adhesive layer of an ion sensor according to a modified example.
Figure 24:
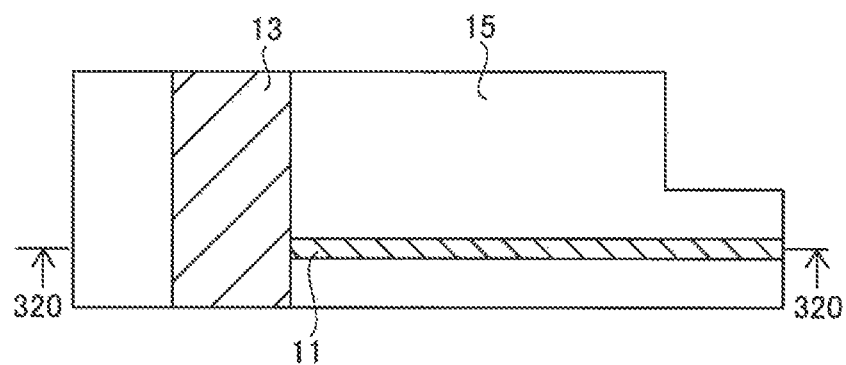
FIG. 24 is a plan view showing an insulating substrate on which a first electrode and an organic phase retaining layer are laminated.
Figure 25:
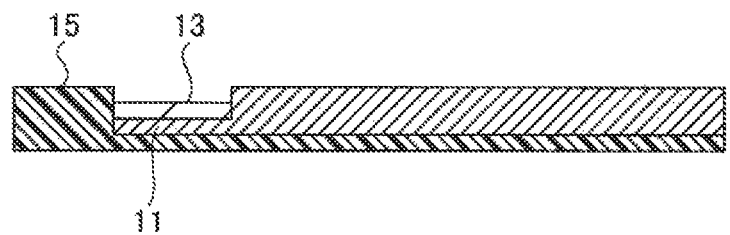
FIG. 25 is a schematic cross-sectional view along the line 320-320 of FIG. 24.

FIG. 18 shows a plan view of the ion sensor 200 of the modified example. FIG. 19 shows a schematic side view of the ion sensor 200. FIG. 20 is a schematic cross-sectional view taken along the line 300-300 of FIG. 18. FIGS. 21 to 25 are exploded views of the ion sensor 200. FIG. 21 is a bottom view of the insulating substrate 16 on which the second electrode 12 is laminated, and FIG. 22 is a schematic cross-sectional view taken along the line 310-310 of FIG. 21. FIG. 23 is a top view of the adhesive layer 17. FIG. 24 is a plan view of the insulating substrate 15 on which the first electrode 11 and the organic phase retaining layer 13 are laminated, and FIG. 25 is a schematic cross-sectional view taken along the line 320-320 of FIG. 24.

As shown in FIGS. 18, 19, and 20, the ion sensor 200 includes a first electrode 11, a second electrode 12, an organic phase retaining layer 13, an insulating substrate 15, an insulating substrate 16, and an adhesive layer 17. The first electrode 11 of the ion sensor 200 is connected to a current measuring unit 22 for measuring the current via a conducting wire 23. The second electrode 12 is connected to a voltage application unit 21 to which a voltage is applied via a conducting wire 24. The voltage application unit 21 and the current measuring unit 22 are connected to each other by a conducting wire 25.

In the ion sensor 200, the adhesive layer 17 is superposed on the insulating substrate 15 (see FIGS. 24 and 25) on which the first electrode 11 and the organic phase retaining layer 13 are laminated at a position lacking the organic phase retaining layer 13, and the insulating substrate 16 on which the second electrode 12 is laminated (see FIGS. 21 and 22) is assembled by overlaying the insulating substrate 16 (see FIGS. 21 and 22) in a direction in which the second electrode 12 is arranged on the lower side. In the assembled ion sensor 200, as shown in FIGS. 18, 19 and 20, the organic phase retaining layer 13 is laminated on the first electrode 11, and the second electrode 12 faces the organic phase retaining layer 13 through a space 34 into which the sample is suctioned. An opening 35 and an opening 36 are provided on the side surface of the ion sensor 200, and the space 34 is an open space. When the user of the ion sensor 200 brings the sample 30 into contact with the opening 35 or the opening 36, the sample 30 is suctioned into the space 34 by capillary force. The measurement of the target ion contained in the sample 30 is performed by the same method as that of the ion sensor 100.

What is claimed is:

1. An ion sensor of current measurement type that measures a current to measure a target ion, comprising:
    an organic phase retaining layer containing an organic phase capable of forming an interface with a sample containing the target ion;
    a first electrode containing a first insertion material including an inorganic compound to which the organic phase retaining layer is laminated; and
    a second electrode arranged to face the organic phase retaining layer and in contact with the sample, wherein
    the first electrode further contains a solid electrolyte,
    the first insertion material and the solid electrolyte of the first electrode are particles, and
    a ratio of an average particle size of the particles of the solid electrolyte to the average particle size of the particles of the first insertion material is 0.001 or more and 0.3 or less.

2. The ion sensor according to claim 1, wherein
    the first electrode further includes an electrode material, and an insertion coating film containing the first insertion material is provided on the electrode material.

3. The ion sensor according to claim 2, wherein the insertion coating film of the first electrode further contains a binder and a conductive agent.

4. The ion sensor according to claim 3, wherein the binder is:
(a) polyvinylidene fluoride,
(b) a mixture containing styrene-butadiene latex and carboxymethyl cellulose,
(c) a mixture containing polyamide, polyimide and carbodiimide,
(d) polytetrafluoroethylene, or
(e) an acrylic emulsion.

5. The ion sensor according to claim 3, wherein the conductive agent is carbon black, acetylene black, ketjen black, carbon nanotubes, graphene, carbon powder, or graphite powder.

6. The ion sensor according to claim 1, wherein the first insertion material is a metal oxide, an oxygen redox material, or a Prussian blue analog.

7. The ion sensor according to claim 1, wherein the first insertion material is an ion-electron conductor.

8. The ion sensor according to claim 7, wherein the first insertion material is the ion-electron conductor for sodium ion, potassium ion or lithium ion.

9. The ion sensor according to claim 1, wherein the first insertion material is a metal oxide; and the metal oxide is $M_xMnO_2$, wherein M indicates Na or K, and x indicates an arbitrary positive number.

10. The ion sensor according to claim 9, wherein x is 0.2 or more and 0.5 or less.

11. The ion sensor according to claim 1, wherein the solid electrolyte is an ion conductive ceramic.

12. The ion sensor according to claim 11, wherein the solid electrolyte is a sodium ion conductive ceramic, a potassium ion conductive ceramic, or a lithium ion conductive ceramic.

13. The ion sensor according to claim 11, wherein the solid electrolyte is β"-alumina or β-alumina.

14. The ion sensor according to claim 1, wherein the first insertion material has a mass of 0.5 times or more and 2 times or less with respect to the solid electrolyte.

15. The ion sensor according to claim 1, wherein the organic phase retaining layer contains an ionophore.

16. The ion sensor according to claim 1, wherein the second electrode includes a second insertion material.

17. The ion sensor according to claim 16, wherein the second insertion material is the same material as the first insertion material; and
the second electrode has the same structure as the first electrode.

18. The ion sensor according to claim 1, wherein the ratio of the average particle size of the particles of the solid electrolyte to the average particle size of the particles of the first insertion material is 0.005 or more and 0.1 or less.

19. The ion sensor according to claim 1, wherein the ratio of the average particle size of the particles of the solid electrolyte to the average particle size of the particles of the first insertion material is 0.01 or more and 0.05 or less.

20. A method for measuring ions used in the ion sensor according to claim 1, the method comprising:
bringing the sample into contact with the organic phase retaining layer and the second electrode;
moving the target ion contained in the sample to the organic phase by applying a voltage between the first electrode and the second electrode; and
measuring a current flowing between the first electrode and the second electrode.

21. The method for measuring ions according to claim 20, wherein
the moving comprises moving the target ion to the organic phase by applying a constant voltage, and
the method further comprises:
obtaining an amount of the target ion based on an amount of electricity obtained by integrating a current value acquired in the measuring the current with an application time of the voltage.

* * * * *